United States Patent
Tang

(10) Patent No.: US 10,846,502 B2
(45) Date of Patent: Nov. 24, 2020

(54) ULTRASONIC FINGERPRINT SENSOR WITH A NON-UNIFORM CONTACT LAYER

(71) Applicant: InvenSense, Inc., San Jose, CA (US)

(72) Inventor: Hao-Yen Tang, San Jose, CA (US)

(73) Assignee: InvenSense, Inc., San Jose, CA (US)

(*) Notice: Subject to any disclaimer, the term of this patent is extended or adjusted under 35 U.S.C. 154(b) by 83 days.

(21) Appl. No.: 16/169,798

(22) Filed: Oct. 24, 2018

(65) Prior Publication Data

US 2019/0325185 A1  Oct. 24, 2019

Related U.S. Application Data

(60) Provisional application No. 62/660,870, filed on Apr. 20, 2018.

(51) Int. Cl.
*G06K 9/00* (2006.01)
*A61B 5/1172* (2016.01)

(52) U.S. Cl.
CPC .......... *G06K 9/0002* (2013.01); *A61B 5/1172* (2013.01); *G06K 9/001* (2013.01)

(58) Field of Classification Search
None
See application file for complete search history.

(56) References Cited

U.S. PATENT DOCUMENTS

| | | | |
|---|---|---|---|
| 10,198,610 B1* | 2/2019 | Yousefpor | G06K 9/0008 |
| 2017/0090028 A1* | 3/2017 | Djordjev | G01S 15/89 |
| 2017/0311924 A1 | 11/2017 | Sudol | |
| 2017/0323133 A1 | 11/2017 | Tsai | |
| 2017/0326594 A1 | 11/2017 | Berger et al. | |
| 2018/0129849 A1* | 5/2018 | Strohmann | G06F 21/32 |
| 2018/0357457 A1* | 12/2018 | Rasmussen | G06K 9/0002 |

OTHER PUBLICATIONS

ISA/EP, International Search Report and Written Opinion for International Application # PCT/US2019/027711, pp. 1-10, dated Jul. 5, 2019.

* cited by examiner

*Primary Examiner* — Duane N Taylor, Jr.

(57) ABSTRACT

A sensor device comprising a two-dimensional array of ultrasonic transducers, wherein the two-dimensional array of ultrasonic transducers is substantially flat, a non-uniform contact layer overlying the two-dimensional array of ultrasonic transducers, and a sensor processor is described. The sensor device is configured to: transmit ultrasonic signals using the two-dimensional array of ultrasonic transducers for reflection from an object in contact with the non-uniform contact layer, wherein the ultrasonic signals traverse the non-uniform contact layer, receive reflected ultrasonic signals at the two-dimensional array of ultrasonic transducers, obtain non-uniformity data characterizing the non-uniform contact layer, control operating parameters of the sensor device based on the non-uniformity data, and generate an image of the object in contact with the non-uniform contact layer based on the reflected ultrasonic signals, wherein the image is corrected for non-uniformity of the non-uniform contact layer.

21 Claims, 12 Drawing Sheets

ULTRASONIC FINGERPRINT SENSOR WITH A NON-UNIFORM CONTACT LAYER

RELATED APPLICATIONS

This application claims also priority to and the benefit of U.S. Provisional Patent Application 62/660,870, filed on Apr. 20, 2018, entitled "FINGERPRINT SENSOR WITH NON-FLAT AND/OR NON-UNIFORM SURFACE," by Hao-Yen Tang, having assigned to the assignee of the present application, which is incorporated herein by reference in its entirety.

BACKGROUND

Fingerprint sensors have become ubiquitous in mobile devices as well as other applications for authenticating a user's identity. They provide a fast and convenient way for the user to unlock a device, provide authentication for payments, etc. Current fingerprint sensors are typically area sensors that obtain a two-dimensional image of the user's finger area presented to the sensor. Different technologies can be used to image the finger such as capacitive, ultrasound, and optical sensing. Once an image is obtained, that image is processed by a matcher to extract features and to compare against stored images to authenticate the user. As such, accuracy of captured images is essential to the performance of image matching for user authentication.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

DESCRIPTION OF EMBODIMENTS

Figure 1A:
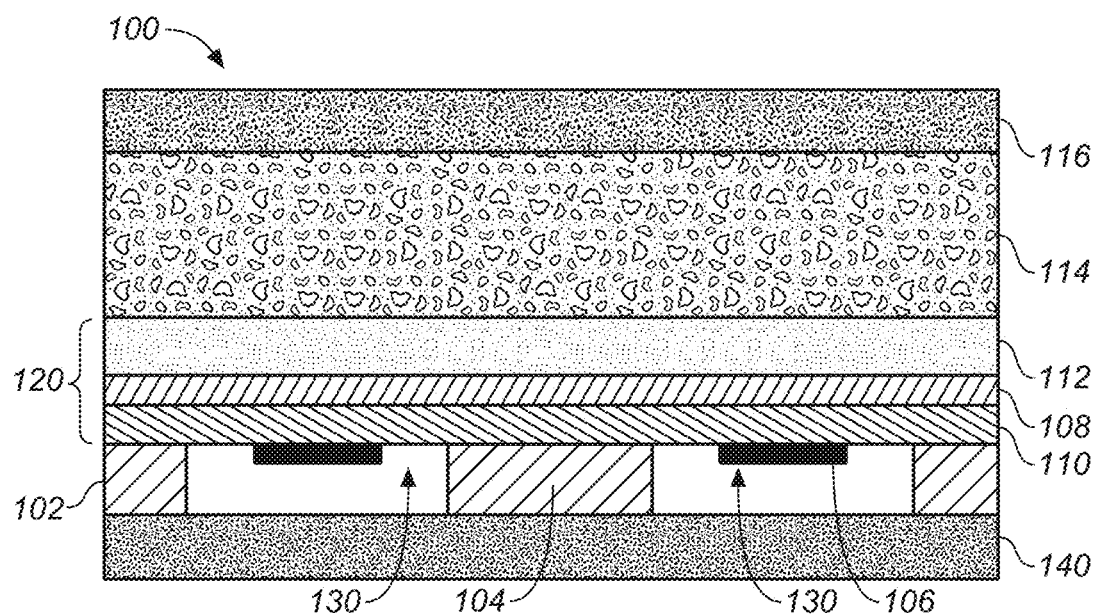
FIG. 1A is a diagram illustrating a piezoelectric micromachined ultrasonic transducer (PMUT) device having a center pinned membrane, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "transmitting," "receiving," "obtaining," "controlling," "generating," "adjusting," "comparing," "selecting," or the like, refer to the actions and processes of an electronic device such as an electrical device.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example fingerprint sensing system and/or mobile electronic device described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

Overview of Discussion

Discussion begins with a description of an example piezoelectric micromachined ultrasonic transducer (PMUT), in accordance with various embodiments. Example arrays including PMUT devices are then described. Example operations of example arrays of ultrasonic transducers (e.g., PMUT devices) are then further described, including the use of multiple PMUT devices to form a beam for capturing a pixel. Examples of the ultrasonic fingerprint sensors having non-uniform contact layers are then described. Examples of correcting for non-uniformity of a non-uniform contact layer in an ultrasonic fingerprint sensor are then described.

Embodiments described herein provide a sensor device including a two-dimensional array of ultrasonic transducers, wherein the two-dimensional array of ultrasonic transducers is substantially flat, a non-uniform contact layer overlying the two-dimensional array of ultrasonic transducers, and a sensor processor. In one embodiment, the non-uniform contact layer includes regions of varying thickness. In one embodiment, the non-uniform contact layer includes a plurality of materials having different acoustic properties.

The sensor device is configured to: transmit ultrasonic signals using the two-dimensional array of ultrasonic transducers for reflection from an object in contact with the non-uniform contact layer, wherein the ultrasonic signals traverse the non-uniform contact layer, receive reflected ultrasonic signals at the two-dimensional array of ultrasonic transducers, obtain non-uniformity data characterizing the non-uniform contact layer, control operating parameters of the sensor device based on the non-uniformity data, and generate an image of the object in contact with the non-uniform contact layer based on the reflected ultrasonic signals, wherein the image is corrected for non-uniformity of the non-uniform contact layer. In one embodiment, the sensor device is further configured to transmit the ultrasonic signals using the two-dimensional array of ultrasonic transducers based on a predefined non-uniformity template.

In one embodiment, the control of the operating parameters includes an adjustment for a difference in time-of-flight of the ultrasonic signals for at least one ultrasonic transducer of the two-dimensional array of ultrasonic transducers. In one embodiment, the adjustment for the difference in the time-of-flight of the ultrasonic signals includes an adjustment of timing parameters of a measurement window for the reflected ultrasonic signals. In one embodiment, the timing parameters of the measurement window are identical for all ultrasonic transducers, and the timing parameters of the measurements window are defined to cover differences in time-of-flight caused by the non-uniform contact layer. In another embodiment, the timing parameters of the measurement window are adapted for a plurality of ultrasonic transducers. In another embodiment, the control of the operating parameters includes an adjustment of timing of transmission of the ultrasonic signals for ultrasonic transducers of the two-dimensional array of ultrasonic transducers. In another embodiment, the control of the operating parameters includes an adjustment for a difference in reflection of the ultrasonic signals for at least one ultrasonic transducer of the two-dimensional array of ultrasonic transducers.

In one embodiment, the sensor device further includes a memory device having stored thereon the non-uniformity data, wherein the sensor device is configured to obtain the non-uniformity data by reading the non-uniformity data from the memory device. In one embodiment, the non-uniformity data includes a time-of-flight register for ultrasonic transducers of the two-dimensional array of ultrasonic transducers. In one embodiment, the time-of-flight register is a time-of-flight map.

In one embodiment, in obtaining the non-uniformity data, the sensor device is further configured to transmit ultrasonic signals for a plurality of ultrasonic transducers of the two-dimensional array of ultrasonic transducers, compare the reflected ultrasonic signals for at least two different time-of-flights for the plurality of ultrasonic transducers, select a time-of-flight for each of the plurality of ultrasonic transducers based on comparing the reflected ultrasonic signals for at least two different time-of-flights for the plurality of ultrasonic transducers, and generate the non-uniformity data including a register of a selected time-of-flight for each of the plurality of ultrasonic transducers.

In one embodiment, the sensor device is further configured to obtain the non-uniformity data at a plurality of times. In one embodiment, the sensor device is further configured to compare the non-uniformity data from the plurality of times and generate a change signal if the compare is outside a predefined range. In one embodiment, the change signal is indicative of a delamination in the sensor device. In another embodiment, the change signal is indicative of a surface defect.

Piezoelectric Micromachined Ultrasonic Transducer (PMUT)

Systems and methods disclosed herein, in one or more aspects provide efficient structures for an acoustic transducer (e.g., a piezoelectric micromachined actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

Embodiments described herein provide ultrasonic fingerprint sensors having non-uniform contact layers. It should be appreciated that different types of ultrasonic fingerprint sensors having different architectures may be utilized herein. For instance, some architectures include an array of ultrasonic transducers (e.g., PMUTs), embodiments of which are described herein. Other architectures may utilize a film-based design. Although embodiments are described herein with respect to an array of ultrasonic transducers, the methods and techniques may be applied to other ultrasonic sensing architectures where the control of the operating parameters of different segments of the sensors can be adjusted separately to correct for the non-uniform contact surface. The embodiments described herein are with respect to sensors with a non-uniform contact layer, but the techniques and principles discussed may in some situations also be used to improve performance of sensors with uniform contact surfaces.

FIG. 1A is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections on the sides or in vias through edge support 102 or interior support 104, electrically coupling lower electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes lower electrode 106, piezoelectric layer 110, and upper electrode 108, where lower electrode 106 and upper electrode 108 are coupled to opposing sides of piezoelectric layer 110. As shown, lower electrode 106 is coupled to a lower surface of piezoelectric layer 110 and upper electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 112 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, epoxy, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 1B:
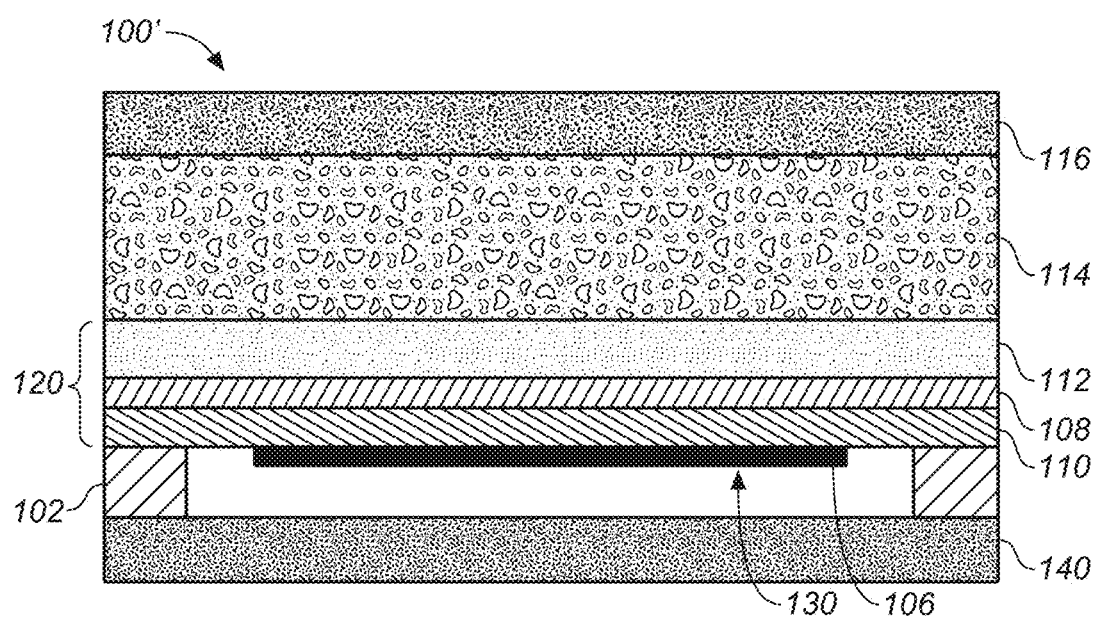
FIG. 1B is a diagram illustrating a PMUT device having an unpinned membrane, according to some embodiments.

FIG. 1B is identical to FIG. 1A in every way, except that the PMUT device 100' of FIG. 1B omits the interior support 104 and thus membrane 120 is not pinned (e.g., is "unpinned"). There may be instances in which an unpinned membrane 120 is desired. However, in other instances, a pinned membrane 120 may be employed.

Figure 2:
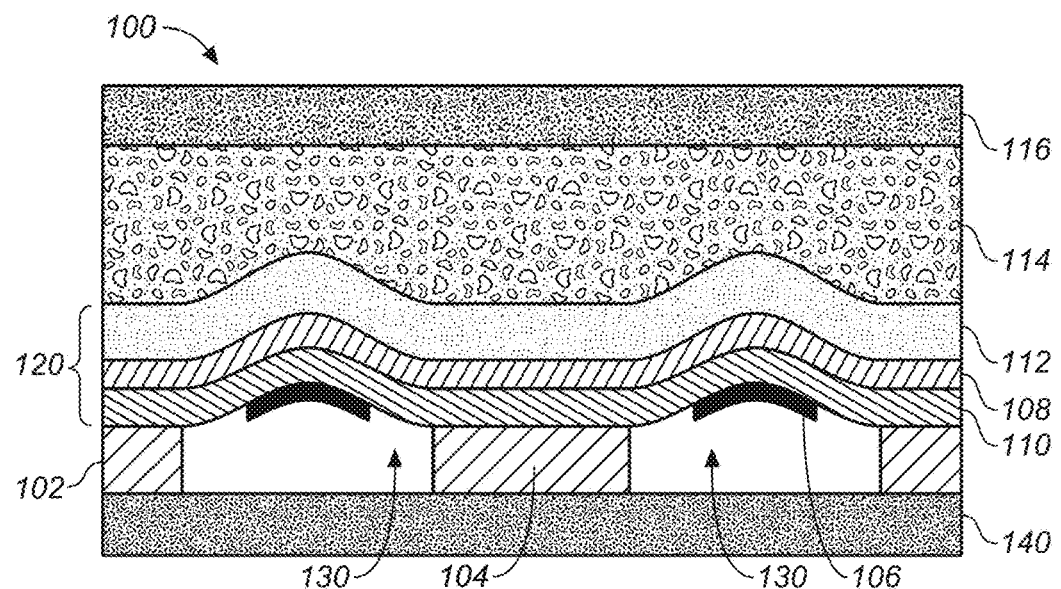
FIG. 2 is a diagram illustrating an example of membrane movement during activation of a PMUT device, according to some embodiments.

FIG. 2 is a diagram illustrating an example of membrane movement during activation of PMUT device 100, according to some embodiments. As illustrated with respect to FIG. 2, in operation, responsive to an object proximate platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to) distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Figure 10:
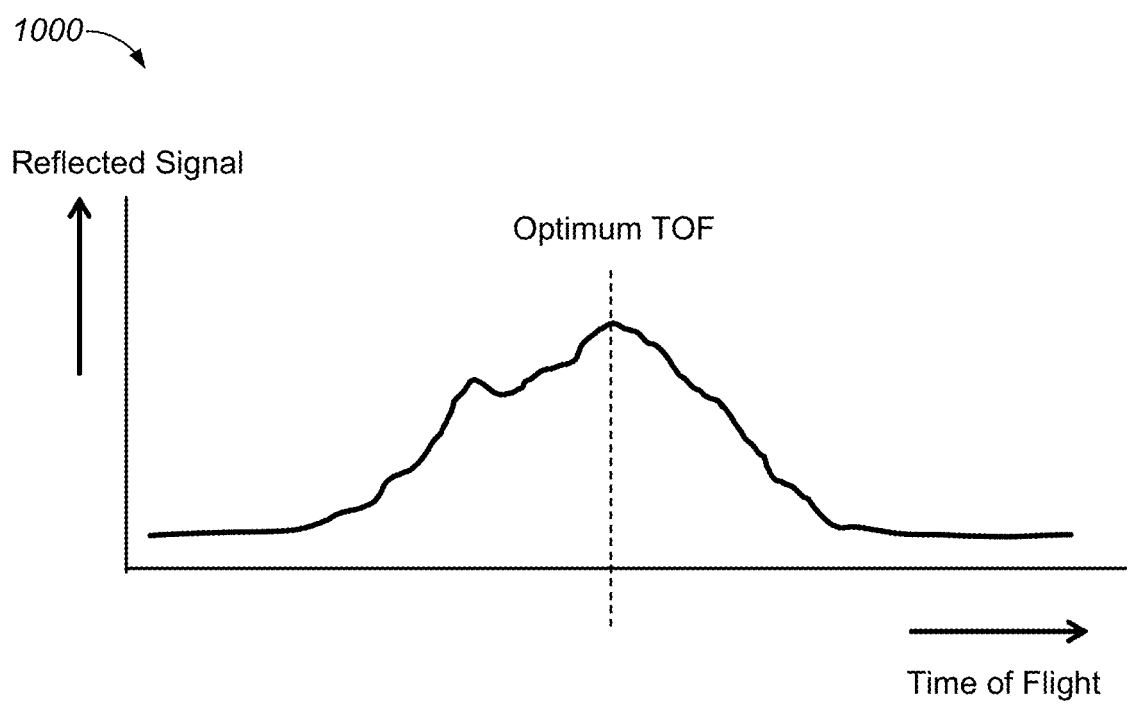
FIG. 10 illustrates an example reflected signal versus time-of-flight curve, according to an embodiment.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, electrode 106 is a patterned electrode and electrode 108 is a continuous electrode. As an example, electrodes 106 and 108 can be comprised of almost any metal layers, such as, but not limited to, Aluminum (Al)/Titanium (Ti), Molybdenum (Mo), etc., which are coupled with and on opposing sides of the piezoelectric layer 110. In one embodiment, PMUT device also includes a third electrode, as illustrated in FIG. 10 and described below.

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 MRayl, such as, but not limited to, plastic, resin, rubber, Teflon, epoxy, etc. In another example, the platen layer 116 can comprise various materials having a high acoustic impedance (e.g., an acoustic impendence greater than 10 MiRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$ Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, MN, Titanium nitride (TiN), Silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., Aluminum (Al)/ Titanium (Ti), Molybdenum (Mo), etc.) patterned to form electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, electrode 108 can be formed as a continuous layer providing a ground plane in contact with mechanical support layer 112, which can be formed from silicon or other suitable mechanical stiffening material. In still other embodiments, the electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

Figure 3:
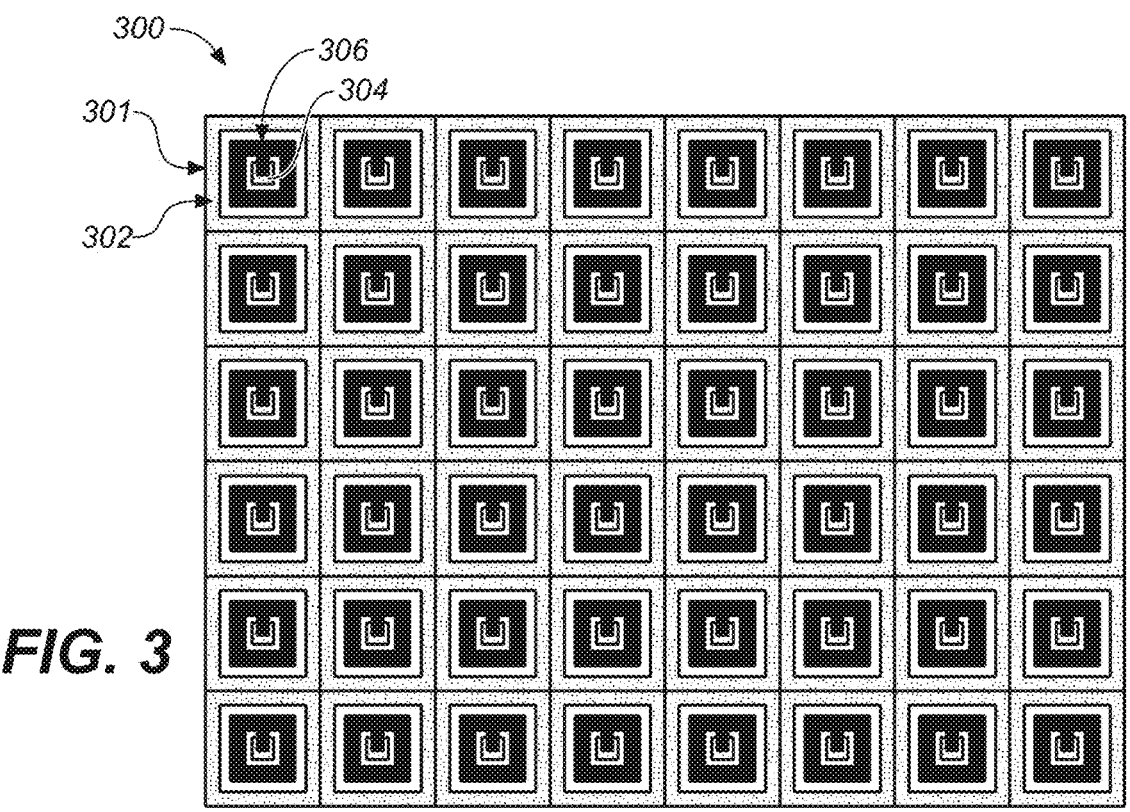
FIG. 3 illustrates an example array of square-shaped PMUT devices, according to some embodiments.

FIG. 3 illustrates an example two-dimensional array 300 of square-shaped PMUT devices 301 formed from PMUT devices having a substantially square shape similar to that discussed in conjunction with FIGS. 1A, 1B, and 2. Layout of square surrounding edge support 302, interior support 304, and square-shaped lower electrode 306 surrounding the interior support 304 are illustrated, while other continuous layers are not shown for clarity. As illustrated, array 300 includes columns of square-shaped PMUT devices 301 that are in rows and columns. It should be appreciated that rows or columns of the square-shaped PMUT devices 301 may be offset. Moreover, it should be appreciated that square-shaped PMUT devices 301 may contact each other or be spaced apart. In various embodiments, adjacent square-shaped PMUT devices 301 are electrically isolated. In other embodiments, groups of adjacent square-shaped PMUT devices 301 are electrically connected, where the groups of adjacent square-shaped PMUT devices 301 are electrically isolated.

In operation, during transmission, selected sets of PMUT devices in the two-dimensional array can transmit an acoustic signal (e.g., a short ultrasonic pulse) and during sensing, the set of active PMUT devices in the two-dimensional array can detect an interference of the acoustic signal with an object (in the path of the acoustic wave). The received interference signal (e.g., generated based on reflections, echoes, etc. of the acoustic signal from the object) can then be analyzed. As an example, an image of the object, a distance of the object from the sensing component, a density of the object, a motion of the object, etc., can all be determined based on comparing a frequency and/or phase of the interference signal with a frequency and/or phase of the acoustic signal. Moreover, results generated can be further analyzed or presented to a user via a display device (not shown).

Figure 4:
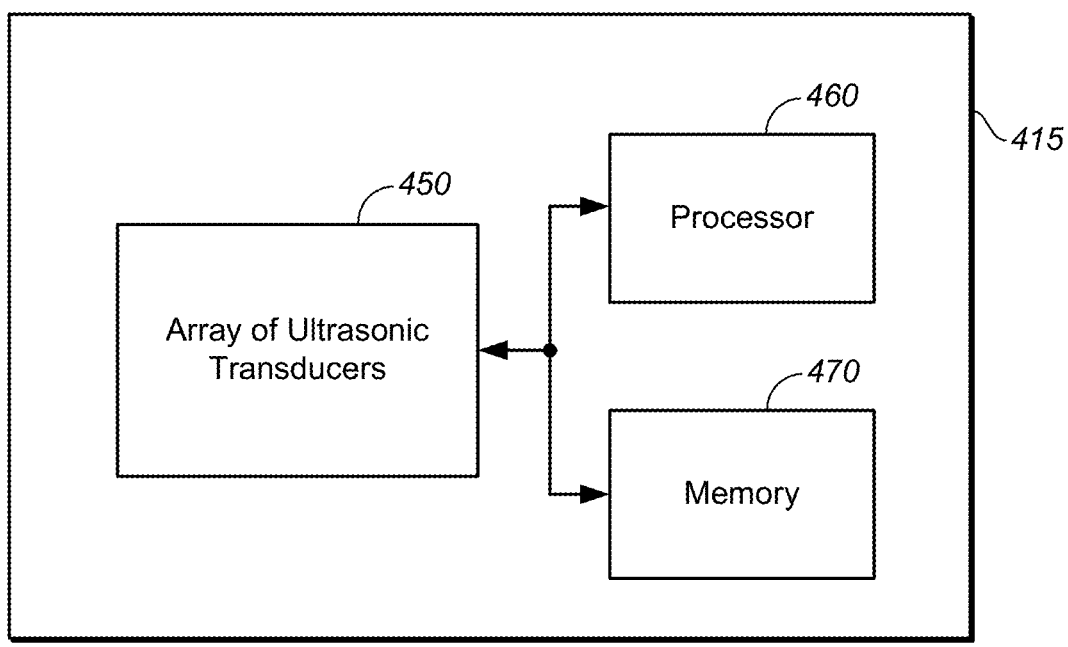
FIG. 4 illustrates an example fingerprint sensor, in accordance with various embodiments.

FIG. 4 illustrates an example fingerprint sensor 415, in accordance with various embodiments. In one embodiment, fingerprint sensor 415 includes an array 450 of ultrasonic transducers (e.g., PMUT devices), a processor 460, and a memory 470. In various embodiments, processor 460 performs certain operations in accordance with instructions stored within memory 470. It should be appreciated that components of fingerprint sensor 415 are examples, and that certain components, such as processor 460 and/or memory 470 may not be located within fingerprint sensor 415. For example, always-on circuitry or system circuitry may include a processor and/or memory for performing certain operations.

In one embodiment, fingerprint sensor 415 includes processor 460 for performing the pixel capture, where pixel capture is performed using subsets of ultrasonic transducers (e.g., PMUTs) of fingerprint sensor 415. In other embodiments, processor 460 can perform at least some signal analysis, e.g., thresholding, to determine whether an object has interacted with fingerprint sensor 415. In other embodiments, processor 460 can analyze captured pixels and determine whether the object has characteristics of finger, e.g., a pattern resembling the ridge/valley pattern of a fingerprint. In other embodiments, processor 460 can capture an image of the fingerprint and forward it to a processor of system circuitry for further analysis.

While the embodiment of FIG. 4 includes processor 460 and memory 470, as described above, it should be appreciated that various functions of processor 460 and memory 470 may reside in other components of an electronic device. Moreover, it should be appreciated that processor 460 may be any type of processor for performing any portion of the described functionality (e.g., custom digital logic).

Example Ultrasonic Sensor Having a Non-Uniform Contact Layer Fingerprint sensors are used in electronic devices for user authentication, such as mobile electronic devices, building locks, automobile locks, etc. In many situations, the surface area of the fingerprint sensor needs to be as flat and as uniform as possible in order to obtain a good fingerprint. However, in some situation it may be desirable to have a non-flat or non-uniform fingerprint surface. For example, when a fingerprint sensor is mounted on the back of a mobile phone, a concave form or structured surface may help guide the user's finger to the correct position on the FP sensor. In other situations, the design employs a non-flat form factor, such as a convex button, a rounded door knob or automobile handle. Some designs may require a smooth surface, while other designs may require a rough or textured surface.

Currently, there are different technologies employed by fingerprint sensors for obtaining a fingerprint, including ultrasonic sensing, capacitive sensing, and optical sensing. For instance, for capacitive sensing and optical sensing to perform properly, the sensing layer must be parallel with the contact layer. Otherwise, the signals received may be distorted in a way that precludes proper imaging. In particular, for a capacitive or optical fingerprint sensor to image through a non-uniform surface, the capacitive or optical fingerprint sensor would be required to be specially manufactured to conform to the non-uniform surface. However, the tailored manufacture of fingerprint sensors is a costly endeavor, impacting the adoption of such tailored fingerprint sensors within commodity devices.

Embodiments described herein provide an ultrasonic fingerprint sensor comprising a substantially flat two-dimensional array of ultrasonic transducers and a non-uniform contact layer overlying the two-dimensional array, where the imaging operation is performed through the non-uniform contact layer. As used herein, the term "substantially" means mostly, primarily, or completely. In particular, the ultrasonic fingerprint sensor described herein can operate using a two-dimensional array of ultrasonic transducers that is capable of sensing through a uniform or non-uniform contact layer without having to modify the two-dimensional array of ultrasonic transducers. Embodiments provided herein control the operating parameters of the ultrasonic fingerprint sensor to correct for the non-uniformity of the non-uniform contact layer, generating a corrected image. Although embodiments are described with respect to an array of ultrasonic transducers, the methods and techniques may be applied to other ultrasound sensing architectures where the control of the operating parameters of different segments of the sensors can be adjusted separately to correct for the non-uniform contact surface. As utilized herein, a non-uniform contact surface is non-uniform with respect to the shape (e.g., non-flat) or material composition of the contact surface, or a combination thereof.

Figure 5A:
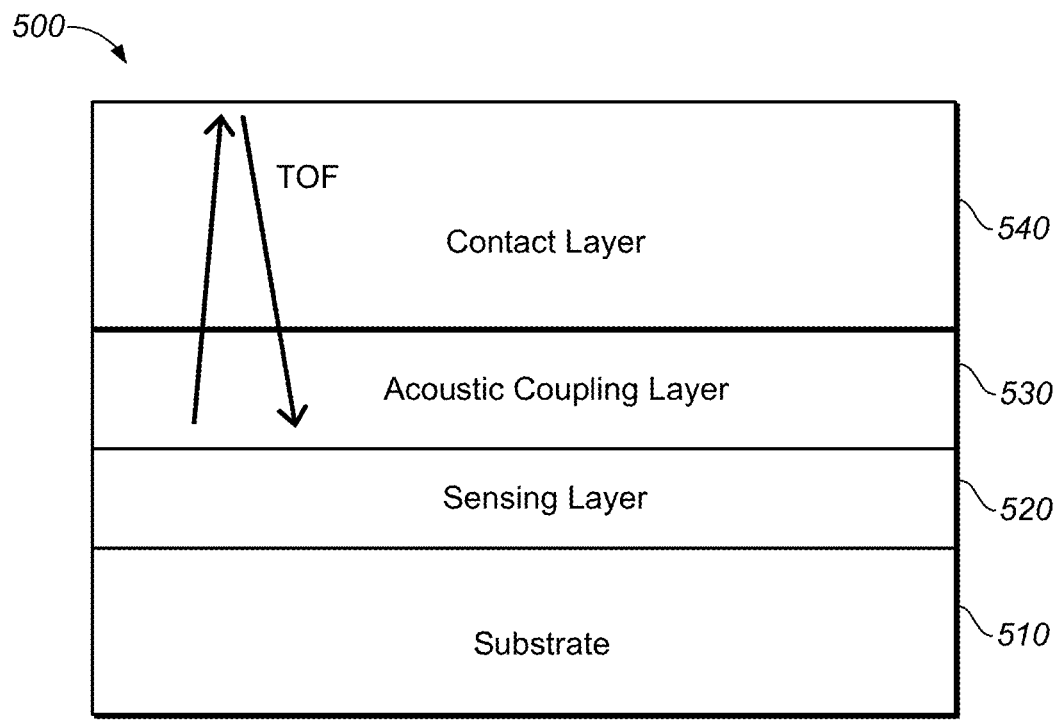
FIG. 5A illustrates a cross section view of an ultrasonic fingerprint sensor, illustrating time-of-flight (ToF) of the transmission of an ultrasonic signal and the receipt of the reflected ultrasonic signal, according to an embodiment.

FIG. 5A illustrates a cross section view of an ultrasonic fingerprint sensor 500, illustrating time-of-flight (ToF) of the transmission of an ultrasonic signal and the receipt of the reflected ultrasonic signal, according to an embodiment. As illustrated, ultrasonic fingerprint sensor 500 includes several different layers. Ultrasonic fingerprint sensor 500 includes an active sensing layer 520 on top of a substrate 510. The active sensing layer 520 may use various techniques to sense or detect the fingerprint, such as e.g. acoustic or ultrasonic techniques. For an ultrasonic fingerprint sensor, the sensing layer may comprise an array of ultrasonic transducers (e.g., PMUTs 100 of FIG. 1A or PMUTs 100' of FIG. 1B) that may be used emit and detect ultrasonic waves. An acoustic coupling layer 530 may be used between the sensing layer 520 and the contact layer 540 onto which the user puts his or her finger. It should be appreciated that in some embodiments, contact layer 540 and acoustic coupling layer 530 are a single layer. In other embodiments, an ultrasonic fingerprint sensor including separate signal transmission and signal detection layers may be used.

Figure 5B:
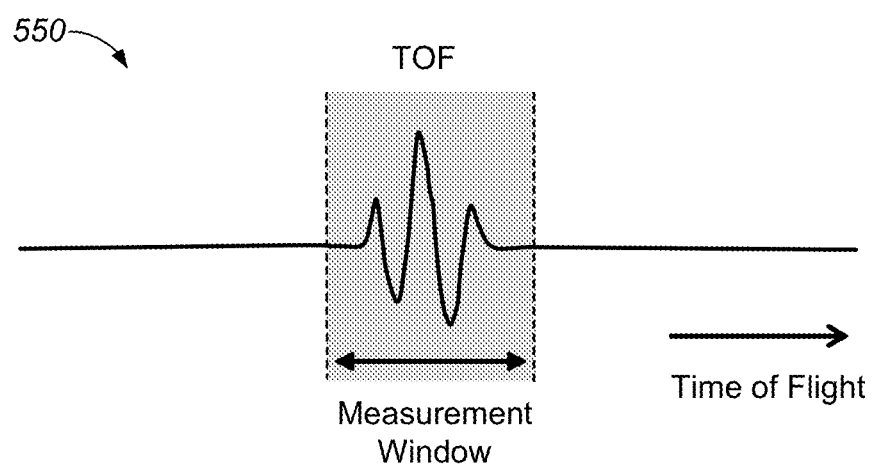
FIG. 5B illustrates an example measurement window for receiving the reflected ultrasonic signal, according to an embodiment.

In an ultrasonic fingerprint sensor 500, the acoustic waves travel from the sensing layer 520 through the coupling layer 530 to the top of the contact layer 540, interact with the object on the surface (e.g., a finger), and may then be reflected back to the sensing layer 520, thereby again traversing the coupling layer 530. The time from the emission of the waves to the detection of the waves is the time-of-flight (ToF) and depends on the acoustic properties and thicknesses of the different layers. Due to acoustic impedance differences of the different layers, multipath reflections, and other factors, the ultrasonic transducers may measure many different signals in addition to the signals directly reflected from the object on the surface. In order to select the signal of interest, i.e., the signal from waves directly reflected from the object on the surface, a measurement window is used. FIG. 5B illustrates an example measurement window 550 for receiving the reflected ultrasonic signal, according to an embodiment.

The measurement windows may be determined based on the acoustic properties and thicknesses of the different layers. It should be appreciated that FIG. 5B shows only the signal of interest, while in practice this signal is combined with the undesired signal from the reflection of other layers and impurities (single-path or multi-path). To obtain a quality fingerprint image with as high as possible signal-to-noise (SNR) and or contrast-to-noise (CNR) ratios, the positioning and size of the measurement window is critical.

Figure 6A:
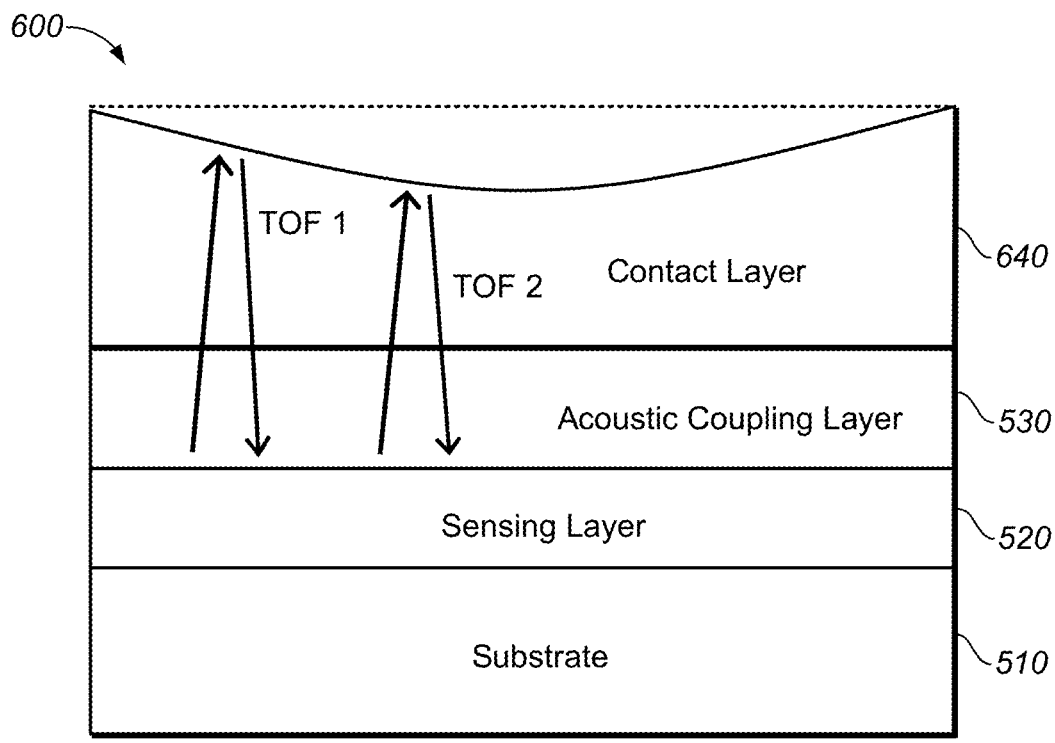
FIG. 6A illustrates a cross section view of an ultrasonic fingerprint sensor comprising a non-uniform contact layer, according to embodiments.
Figure 6B:
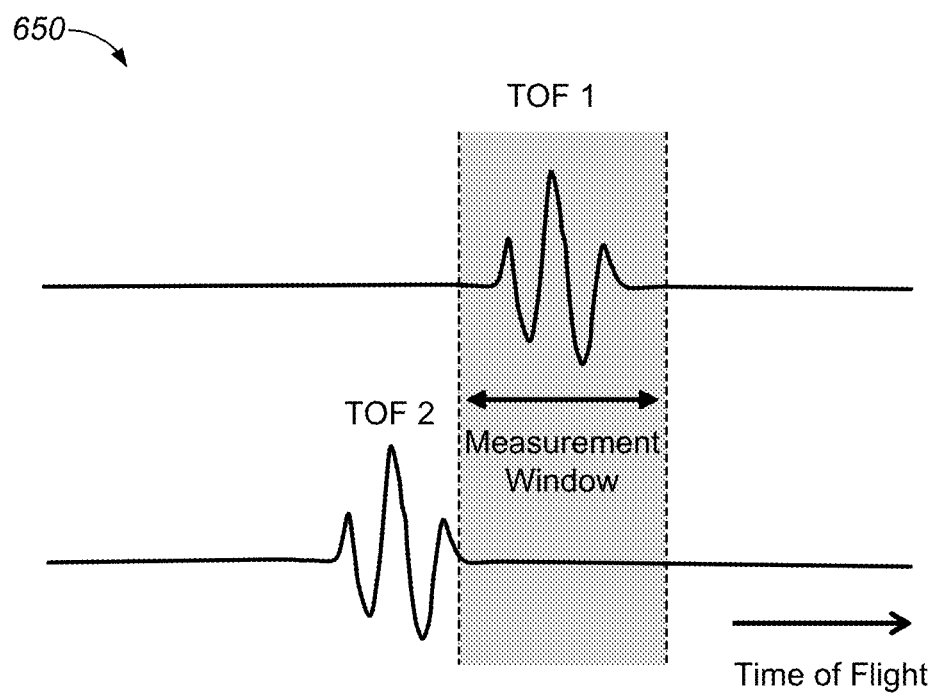
FIG. 6B illustrates an example of two measurement windows for receiving reflected ultrasonic signals at an ultrasonic fingerprint sensor comprising a non-uniform contact layer, according to embodiments.
Figure 7:
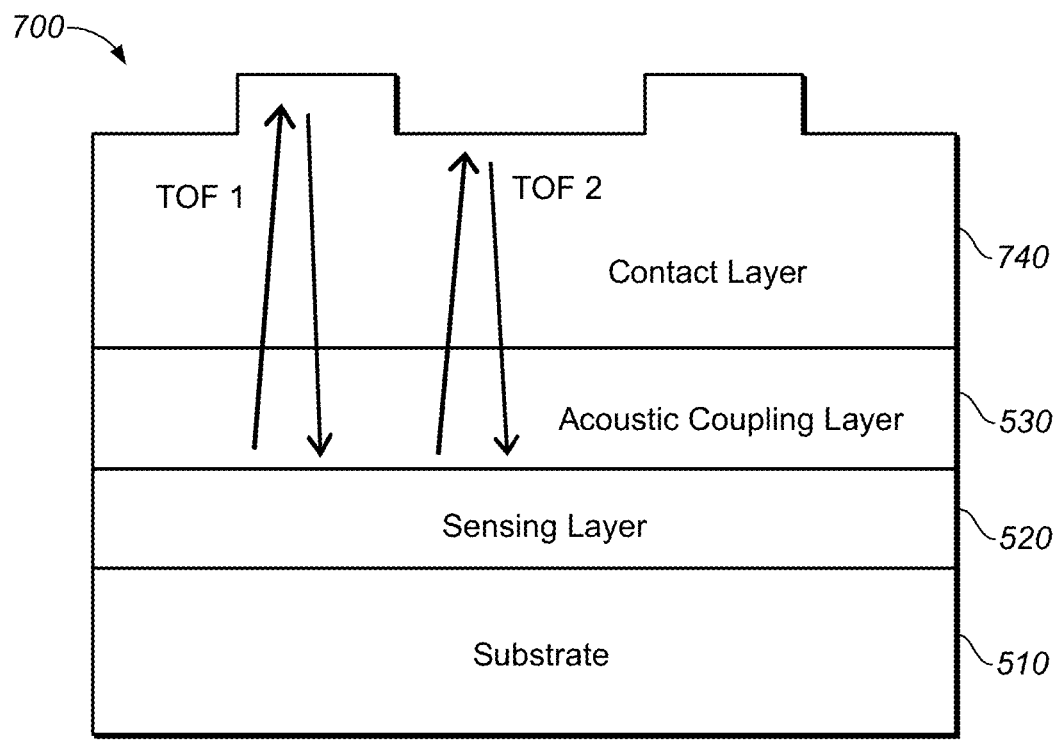
FIG. 7 illustrates a cross section view of an ultrasonic fingerprint sensor comprising a non-flat contact layer, according to embodiments.

When the contact layer is uniform and the sensing layer and contact layer are substantially flat and parallel, as illustrated in FIG. 5A, the selected ToF (range) for best performance is essentially identical for all ultrasonic transducers. The same measurement window settings can therefore be applied to all transducers. Even if there is a slight variation in the ToF of different transducers or different segments of the sensor, a single measurement window may be defined that works well enough for all transducers. However, when the ToF changes are too large, using a single measurement window will degrade the quality of the image. For example, if the contact layer is not flat, but rather a gradient-like structure (e.g., convex or concave) as indicated in contact layer 640 of ultrasonic fingerprint sensor 600 of FIG. 6A, or step-like structure as in contact layer 740 of ultrasonic fingerprint sensor 700 of FIG. 7, or a combination thereof, the length of the traveled path of the ultrasound waves for different transducers of different sections of the sensors varies. Therefore, a single measurement window to cover the large differences in ToF will not work in practice because too much undesired signal would be measured and would therefore decrease the SNR and/or CNR. Thus, for fingerprint sensors with a not-flat contact surface an adaptive ToF method can be used that corrects for the non-uniform effects. FIG. 6B illustrates an example of two measurement windows 650 for receiving reflected ultrasonic signals at an ultrasonic fingerprint sensor comprising a non-uniform contact layer, according to embodiments.

In an example adaptive ToF method, first the optimal ToF to obtain the desired performance is determined for different ultrasonic transducers or different sections of the sensor. Next, a ToF map, ToF listing, or ToF index is created which links the optimum TOF to the different transducers and or segments of the sensor. The TOF map, listing, or index is then used to control the measurement window setting for the different transducers/pixels. The linking may be based on the location of the transducers. For example, a ToF map can be created, where groups of transducers having ToF values within a range are created, allowing for grouped control of the measurement windows for each group. When the ToF information is used to control the measurement window, in general the timing of the transmission of the ultrasonic waves from the different transducers or different section is not adapted. In other embodiments, instead of controlling the measurement window, the transmission timing of the ultrasonic waves may be adapted to correct for the non-uniform contact surface.

Figure 9:
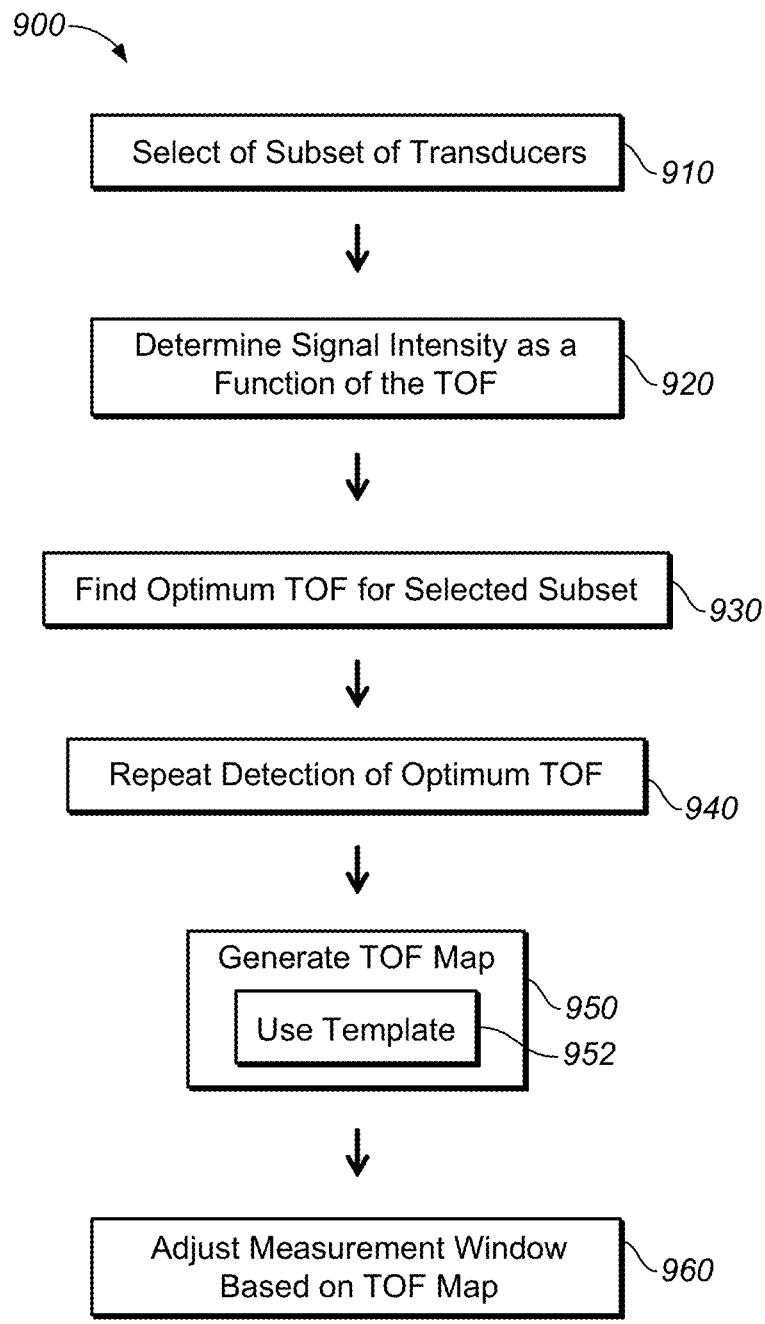
FIG. 9 illustrates a flow chart of an example method of generating a time-of-flight map, according to embodiments.

FIG. 9 illustrates a flow chart 900 of an example method of generating a time-of-flight map, according to embodiments. In procedure 910, a subset of ultrasonic transducers is selected. At procedure 920, the ToF may be determined for each ultrasonic transducer, or may be determined for a plurality of ultrasonic transducers grouped together. For the selected subset, the ultrasonic transducers will emit the acoustic waves and the reflected signal is measured over the complete range of ToF that is of interest, which will account for the expected difference in ToF due to the non-uniform surface. Based on the measurement of the signal over the complete range, as shown at procedures 930 and 940 the optimum ToF is determined. At procedure 950, a ToF map is generated. In one embodiment, as shown at procedure 952, a template is used. At procedure 960, the measurement window is adjusted based on the ToF map.

FIG. 10 illustrates an example reflected signal versus time-of-flight curve 1000, according to an embodiment. The ToF curve represents the measured signal at at least two different ToFs. The ToF curve may be obtained by emitting ultrasonic waves and then measuring the reflected signal over time in a single sweep. Alternatively, the ToF curve may be derived from a plurality of measurement where for each measurement the measurement window is selected around a different central ToF, which is varied to cover the complete ToF range of interest. The ToF curve may be acquired under different operating conditions, such as e.g. at different operating temperatures. Consequently, the ToF adaptation may be performed as a function of the different operating conditions. For example, the adaptation is varied as the operating temperature of the sensor changes. Alternatively, the adaptation parameters may be averaged over the different operating conditions, or a setting may be selected that gave satisfactory performance over the range of operating conditions. Based on the ToF curve and a comparison of the measured signals at different ToFs, a ToF can be selected for optimum performance, and this ToF is referred to as the optimum ToF. This selection can be done for each of the different transducers or different sections. If the contribution of the signal of interest to the total signal is larger than the undesired signal, the optimum ToF will be at the maximum of the signal vs ToF curve. This is also partly due to the fact that the undesired signal contains reflection from different layers and multi-path reflection, which will be spread out over a large ToF range. The signal curve may have local maxima due to specific reflection preferences. The contribution of the signal of interest to the total signal may not be sufficiently dominant so that the optimum TOF corresponds to the maximum TOF. In some situations, the signal of interest may result in a local maximum different from the global maximum, and in this situation, the ToF of the local maximum may be used for the optimum ToF. In some situations, the optimum TOF may be shifted by a certain time compared the global maximum or compared to a local maximum. The shift to a higher ToF may be referred to as a delayed ToF. The use of a delayed ToF may be referred under certain situation, for example, to obtain better performance over a larger temperature range. In some situation, this ToF calibration procedure may be performed with or without an object on the contact surface, since the object would only affect the signal intensity, and not the ToF of the reflected signals. For some objects, the waves may traverse further into the object before being reflected, thereby increasing the ToF which may further contribute to a spreading of the ToF curve. Therefore, in some embodiments of the invention, the ToF calibration procedure will only be performed when it is confirmed that there is no object on the contact surface. This means that a step would be introduced before the first step of FIG. 9, which consists of determining whether an object is present on the surface.

Once the optimum ToF has been determined for all the subsets of ultrasonic transducers of interest, for example covering the complete sensor surface, a ToF map can be produced. In one embodiment, the optimum ToF may be stored for each of the subsets, e.g., for each of the ultrasonic transducers. The ToF map may be smoothed, or otherwise filtered, by comparing neighboring subsets. The smoothing may be based on knowledge about the form or shape of the surface, and how much the surface would change over a certain distance. This can be translated in a maximum change in ToF over the same distance. The knowledge about the form or shape may be in the form of a template characterizing the shape of the surface.

Figure 11A:
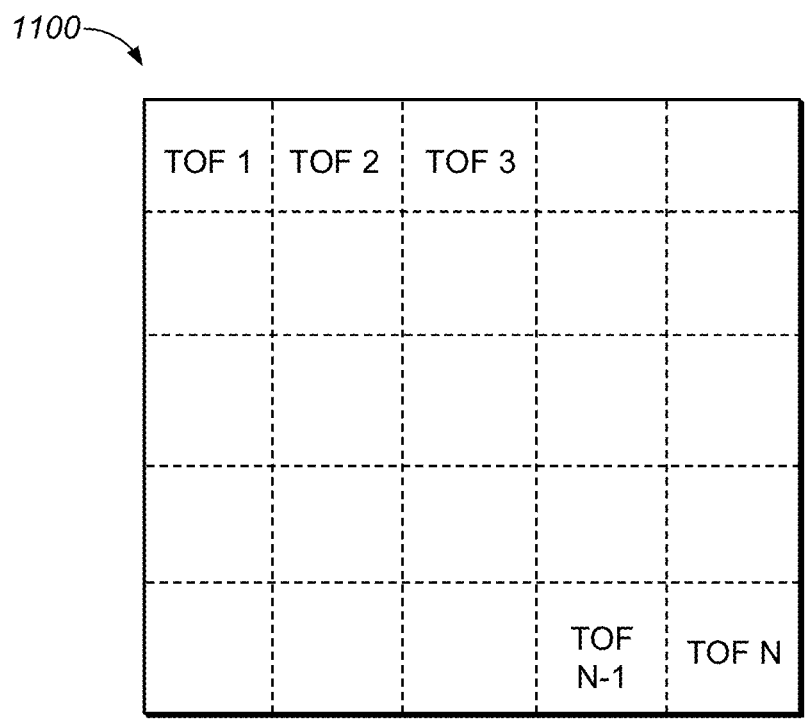
FIGS. 11A and 11B illustrate examples of time-of-flight grouping maps, according to embodiments.
Figure 11B:
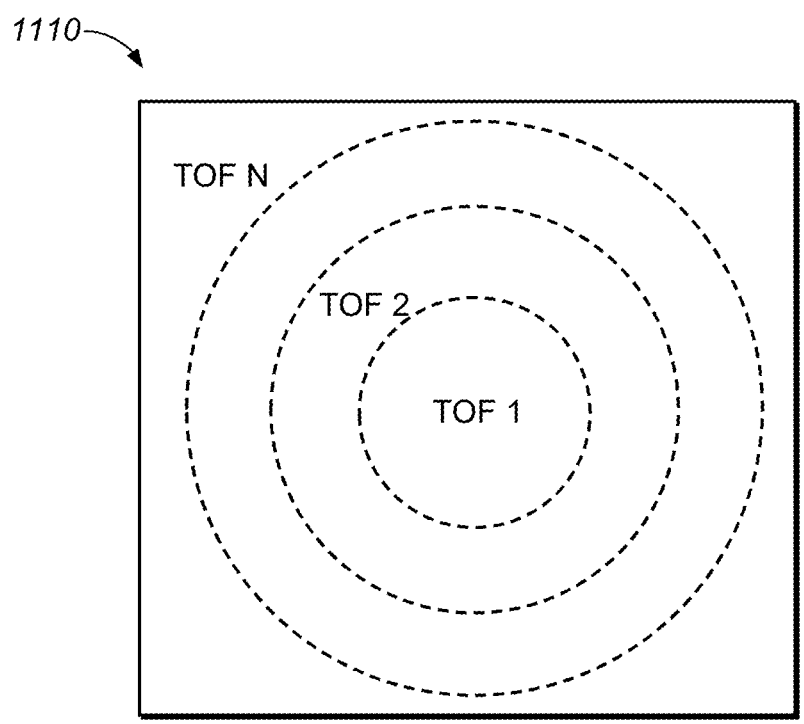

FIGS. 11A and 11B illustrate examples of time-of-flight grouping maps, according to embodiments. Storing the ToF data for each transducer/pixel may require a significant amount of memory. Therefore, in some embodiments, the ToF data is grouped and combined into a compressed data set. For example, as shown in FIG. 11A, a grid ToF map 1100 may be used, and the ToF values within each grid element are average. The grid or template that may be applied may be based on knowledge about the form or shape of the contact surface. The grid or template may be stored in the memory of the sensor. For example, if it is known that the form is concave, the grid ToF map 1110 may be circular, as shown by example in FIG. 11B. The number of grid or template elements may be predefined or may be adaptive. In some embodiments, the grid or template can be detected through a pattern recognition process. For example, a maximum variation of ToF values within one grid element may be defined, and the number of grid elements may then be adapted to accommodate this requirement. The predefined template may be an exact shape definition (e.g. cross-section), or may just indicate the type of class of form, such as e.g. linear circular. For a more complex shape, a more detailed descriptive template may be provided. For example, the surface variation may be due to an embossed or elevated logo, which means the ToF variations would follow the logo shape. A template of the logo may be used to more accurately determine the ToF map. Knowledge about the shape, such as in the form of e.g. a template, may also be used to avoid performing a scan of the transducers to determine the ToF. One or more ToF measurement may be performed within each segment, and if each segment corresponds to a similar thickness, the determined optimal ToF may be applied for the complete segment or part of the sensor.

Once the ToF has been determined and stored, it may be applied to determine the correct operational settings of the measurement windows for the respective subsets of transducers. Regular updates of the ToF map may be performed to make sure the optimum ToF is always available. The update may be regularly in time, or may be triggered by certain events or operational conditions, such as e.g., high motion or acceleration, mechanical shock, (fast) temperature change, extreme temperatures, etc.

In some embodiments, each ultrasonic transducer or group of ultrasonic transducers may be controlled using a determined optimum ToF, where the measurement window is shifted in time according to the optimum ToF. The width of the measurement window may be adapted to the received signal and the variation in the ToF over the selected transducers. The larger the number of transducers that are combined, the higher the possibility that there is a variation of the ToF, and therefore the wider/longer the size of the integration window. A distribution of the optimum ToF values may be determined, and the applied setting may be chosen to comprise a predefined portion or percentage of the distribution. In one embodiment, only a single measurement window size is used, and the ToF investigation is used to determine what the variation in ToF across the sensor surface is, and then the window size is adapted accordingly to capture the desired signal or depending on the ToF distribution.

In some architectures, the measurement window may not be changeable or adaptable for individual transducers, and therefore in some embodiments the measurement window may be divided in a number of sub-windows each having a certain ToF range. Then, based on the optimum ToF for a certain transducer or set of transducers, one or more of the sub-windows are selected corresponding to the optimal ToF. For example, in some architectures, where control of the transducers is collective, in order to capture signals for the entire array of the ultrasonic sensor, the measurement window must be big enough to capture signals over the entire ToF range. In other architectures, where transducers are controllable at a more granular level (e.g., grouped control or individual control), the measurement windows for groups of transducers or individual transducers can be tuned according to the ToF range for the groups of transducers or individual transducers. It should be appreciated that there is a tradeoff between the granular control of transducers and the number of distinct measurement windows. For instance, granular control provides higher quality measurement of received signals, but requires more complicated control mechanisms (e.g., driving circuit, routing, etc.) and might result in higher power consumption. Moreover, it should be appreciated that an ultrasonic fingerprint sensor capable of granular control of transducers utilize the granular control during operations requiring high degrees of precision, while using collective control of the transducers during operations that do not require high degrees of precision.

In the discussion above, the measurements window is varied to correct for the difference in time-of-flight. In alternative embodiments, the measurement window may be constant but the transmission timing may be adapted for the different pixels, so that even with a different ToF, the signal of interest still is measured within the static measurement window. In some embodiments, the transmission timing and the measurement window are both adapted to correct for the differences in ToF. In such embodiments, the ToF map is used to control the transmission of signals from different groups of transducers or individual transducers, such that signals might be transmitted at different times, but are received within a constant measurement window.

The ToF map may also be used to adapt the beam forming operations of the ultrasonic fingerprint sensor. In some embodiments, the ToF may be interpreted or may be converted in to a depth or relief map of the sensor surface. Because the ToF provides information relating the distance between the transducers and the contact surface, this information may also be used to provide a focusing distance. An initial calibration may be required to determine the exact relation between the ToF and the focusing distance, but once this relation is known, it can be applied across the range of ToFs.

Creating a ToF map or gathering ToF data may also be used for different purposes. For example, the ToF data may be used for detection of defects, e.g., (local) delaminations/air bubbles/impurities in the sensor stack or degradation of the contact layer or surface of the contact layer. These types of defects may create high impedance mismatches in the stack resulting in large reflections. As such, signals from transducers that transmit at the location of these defects have smaller ToFs and the defects can therefore be detected using the ToF analysis. In other examples, the ToF data may be used for detection of defects in the contact layer or on the contact surface (e.g., scratches). As such, the ToF analysis or map may be used as a self-test to check for defect that may occur during manufacturing, over time, or after events like shocks or high accelerations or temperature changes (e.g., a delamination test or a surface condition test). The non-uniformity data may be obtained a plurality of times, and then be compared. If this comparison indicates that a change is outside a predefined range or above a predefined threshold, this may indicate a defect or degradation. A signal or interrupt may be generated to inform the system of the defects, the extend of the defects, and the possible influence of the defects on the imaging quality of the sensor. The signal may be representative of the quality of the surface, and the capability to properly image the object. For example, the amount of surface damage may be determined, and the location of the damages may be determined. In some embodiments, the image may be corrected for the non-uniformity, while in other embodiments, correction of the image for the non-uniformity may not be performed or may not be possible.

The discussion above has been focused on dealing with a non-flat surface, which leads to differences in time-of-flight. In a similar manner, methods to correct for non-uniform surfaces can be derived. For example, a non-uniform contact surface may comprise different materials with different acoustic properties.

Figure 8A:
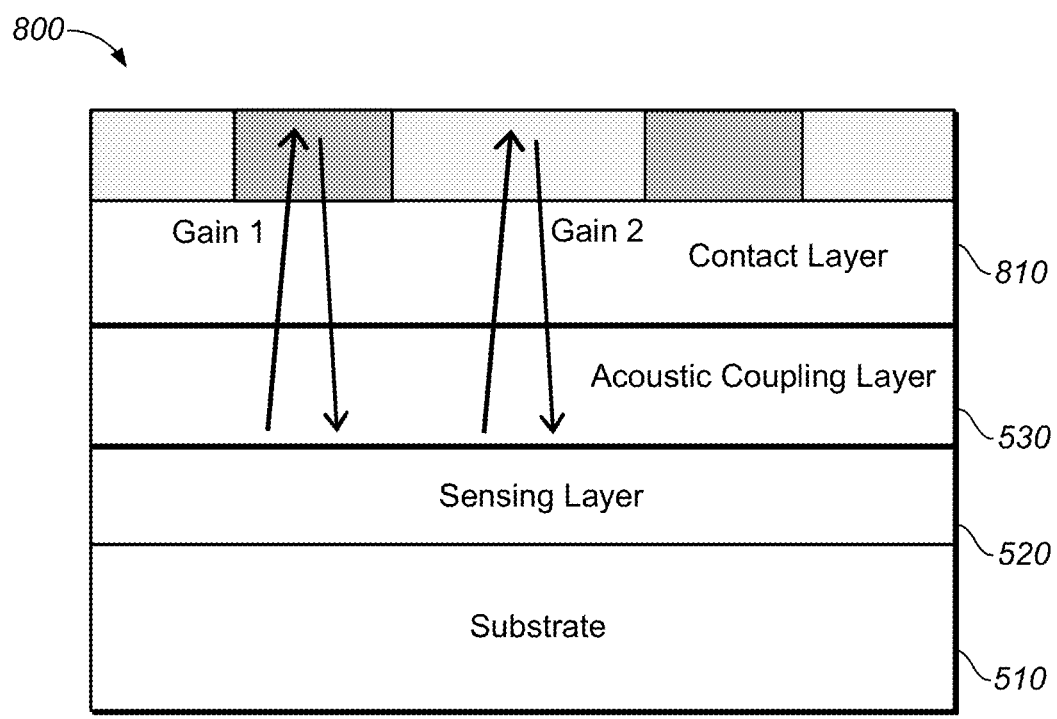
FIG. 8A illustrates a cross section view of an ultrasonic fingerprint sensor comprising a non-uniform contact layer comprising materials having different acoustic properties, according to embodiments.

FIG. 8A illustrates a cross section of an ultrasonic fingerprint sensor 800 comprising a non-uniform contact layer 810 comprising materials having different acoustic properties, according to embodiments. Ultrasonic fingerprint sensor 800 illustrates an example of a contact layer 810 with different top materials. In one embodiment, the different materials are caused by a logo present on top of the contact surface (e.g., different colors, reflections, or other optical effects to create a logo or other design feature). The different materials may lead to different attenuations of the signal, and in order to have a uniform image of the object on the sensor surface, a correction for the different attenuations is required. In one embodiment, the difference in attenuation may be corrected by applying a different gain to the measured signal.

In accordance with various embodiments, a similar strategy as described above in the creation of a ToF map may be applied to create other types of non-uniformity maps, such as a gain map. All the processing and properties of the ToF map as discussed in relation to FIGS. 11A and 11B may also apply to the gain map (e.g. use of grids, templates, . . . ). A difference with the ToF map is that to create the gain map, no object should be present on the contact surface. Thus, before starting the calibration of the gain map, a first stage where it is verified that there is no object on the surface should be performed. Then for each of the subsets, the gain required to create a uniform signal intensity over the sensor surface is determined and mapped. It should be appreciated that embodiments described herein may utilize different types of non-uniformity maps that represent non-uniformity data, such as ToF maps and gain maps.

Figure 8B:
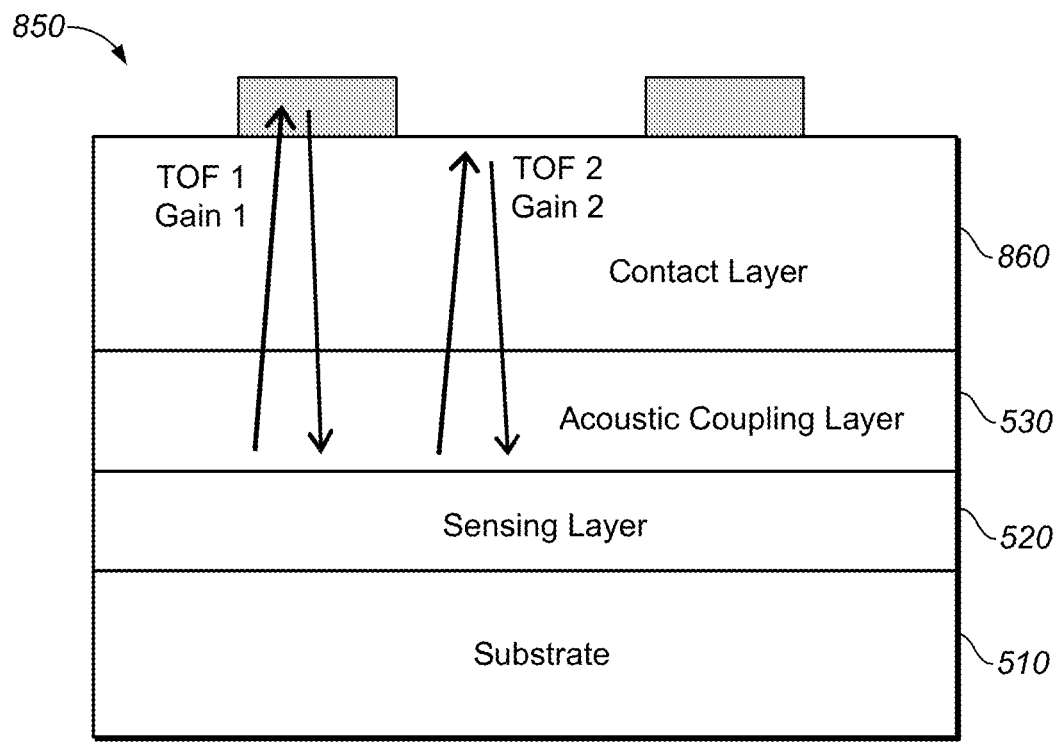
FIG. 8B illustrates a cross section view of an ultrasonic fingerprint sensor comprising a non-uniform contact layer that is non-flat and comprises materials having different acoustic properties, according to embodiments.

FIG. 8B illustrates a cross section view of an ultrasonic fingerprint sensor 850 comprising a non-uniform contact layer 860 that is non-flat and comprises materials having different acoustic properties, according to embodiments. In this example, both techniques of the ToF map and the gain map may be applied, separately or concurrently.

Figure 8C:
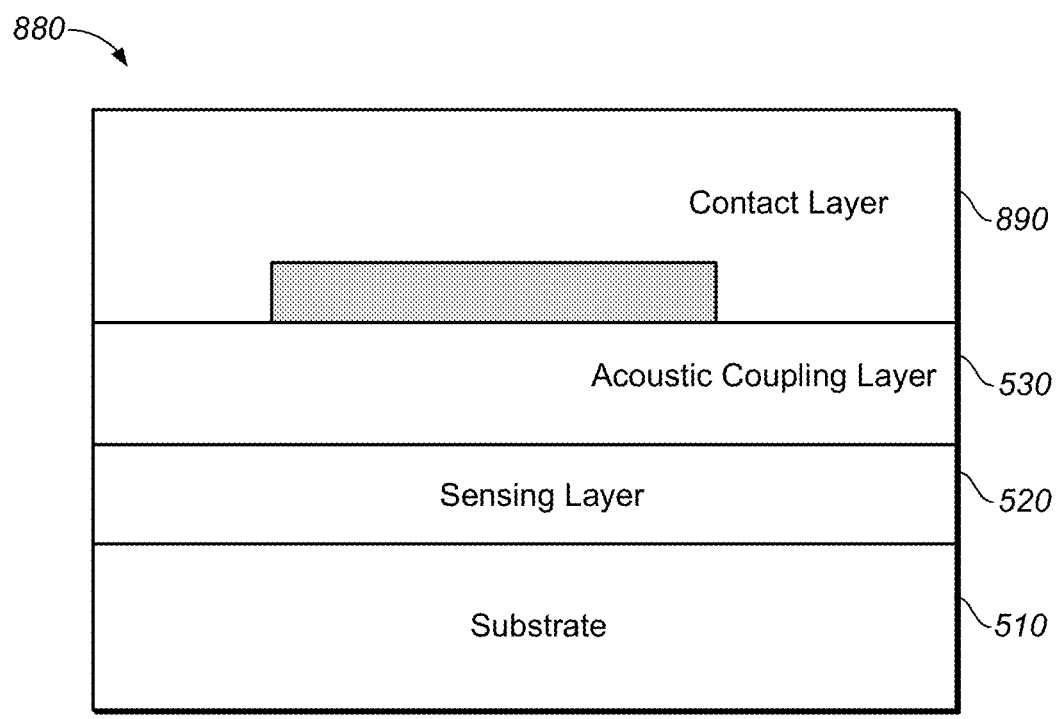
FIG. 8C illustrates a cross section view of an ultrasonic fingerprint sensor comprising a non-uniform contact layer comprising materials having different acoustic properties, according to embodiments.

FIG. 8C illustrates a cross section view of an ultrasonic fingerprint sensor 880 comprising a non-uniform contact layer 890 comprising materials having different acoustic properties, according to embodiments. In this example, both techniques of the ToF map and the gain map may be applied, separately or concurrently.

The various embodiments described herein may be applied to an ultrasonic fingerprint sensor, where the contact layer is non-uniform. The surface may need to have a certain amount of roughness or variation in depth or thickness, before advantages of the techniques disclosure here become of significant importance. For many applications, if the depth/thickness variations are very small, for example, only a few micrometers, the advantage of applying these techniques may be minor. However, in some applications where high precision is required (e.g. banking applications, high security application, . . . ), even the small depth variations are of importance. For example, operation of the ultrasonic fingerprint sensor can be adaptive and use a higher precision mode (e.g., more granular control of transducers) when high precision is required, and use a lower precision mode (e.g., collective control of transducers) during normal operation. The application of the high precision mode may also depend on the available resources and may not be applied when few power and/or computation resources are available. In devices where the device is designed such that the user can feel where the fingerprint sensor is positioned, a certain depth or thickness variation is required so that the user can actually feel the fingerprint sensor. In these use cases, the depth or thickness variation is generally more than 100 micrometers, and often more than 200-300 micrometers. These depth variations typically benefit from the application of the described embodiments in order to improve the performance of the ultrasonic fingerprint sensor. The discussion of depth or thickness variations relates to the distance between the non-flat surface of the contact layer and the generally flat surface of the sensing layer or substrate layer, as shown in the figures. Moreover, embodiments described herein can be used in improving the integration of the signal by adjusting for any alignment discrepancies between the sensor and the contact surface, even where both the sensor and surface are substantially flat. If the ultrasonic fingerprint sensor and the contact surface are not parallel, the described embodiments can be used to correct for the ToF differences.

Figure 12:
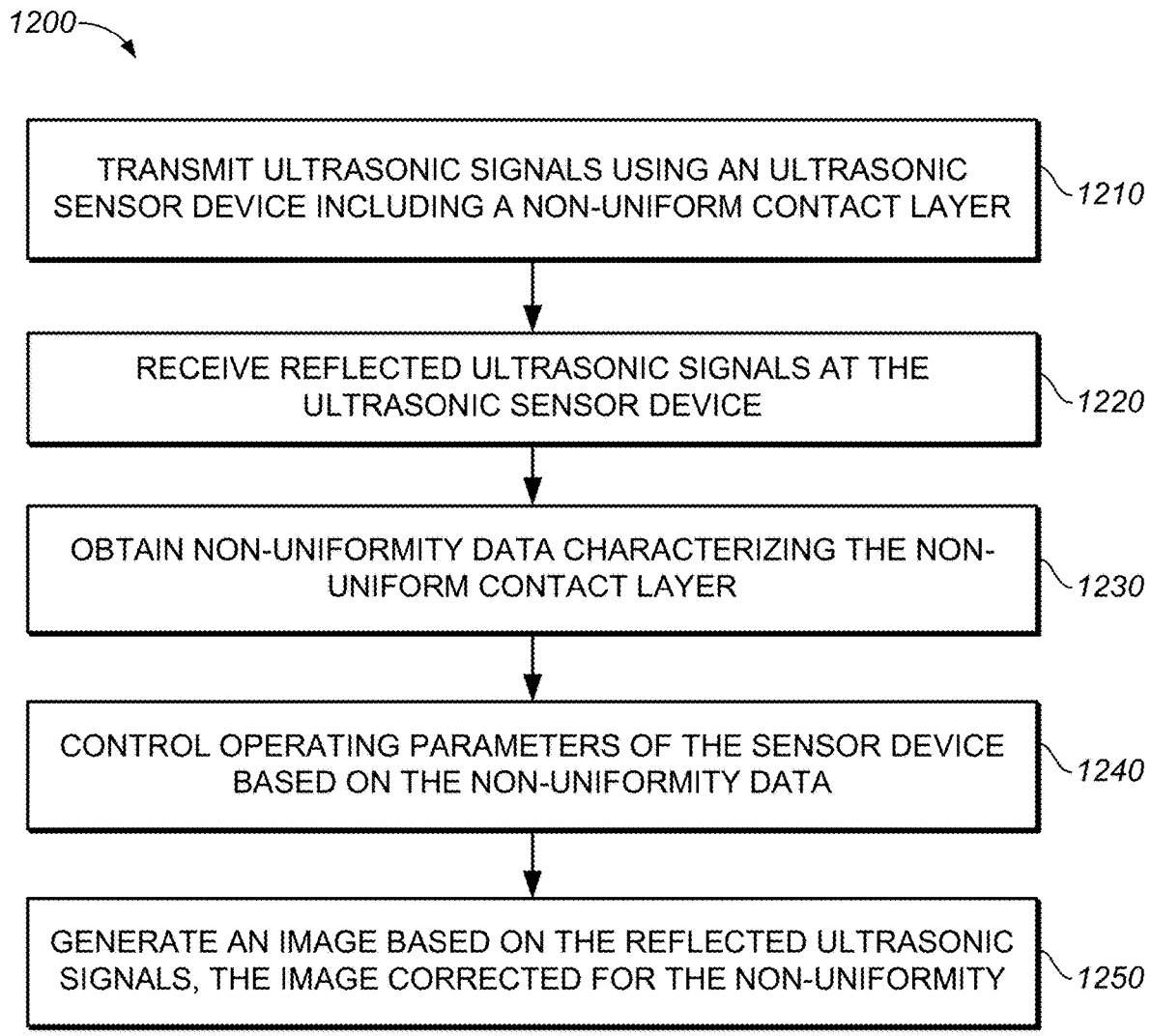
FIG. 12 illustrates a flow diagram of an example method for operating an ultrasonic fingerprint sensor with a non-uniform contact layer, according to an embodiment.
Figure 13:
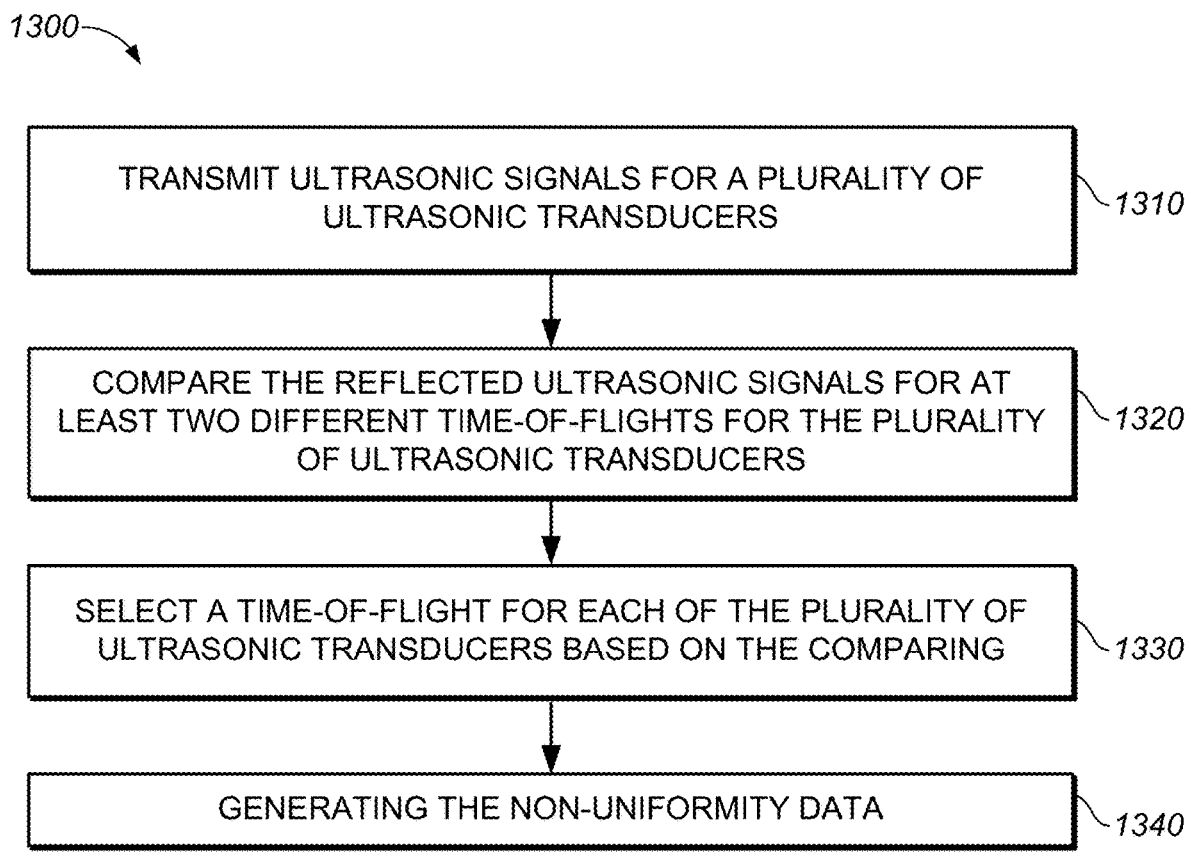
FIG. 13 illustrates a flow diagram of an example method for obtaining non-uniformity data characterizing the non-uniform contact layer, according to an embodiment.

FIGS. 12 and 13 illustrate flow diagrams of example methods for operating a fingerprint sensor comprised of ultrasonic transducers, according to various embodiments. Procedures of these methods will be described with reference to elements and/or components of various figures described herein. It is appreciated that in some embodiments, the procedures may be performed in a different order than described, that some of the described procedures may not be performed, and/or that one or more additional procedures to those described may be performed. The flow diagrams include some procedures that, in various embodiments, are carried out by one or more processors (e.g., a host processor or a sensor processor) under the control of computer-readable and computer-executable instructions that are stored on non-transitory computer-readable storage media. It is further appreciated that one or more procedures described in the flow diagrams may be implemented in hardware, or a combination of hardware with firmware and/or software.

FIG. 12 illustrates a flow diagram 1200 of an example method for operating an ultrasonic fingerprint sensor with a non-uniform contact layer, according to an embodiment. At procedure 1210 of flow diagram 1200, ultrasonic signals are transmitted using an ultrasonic sensor device for reflection from an object in contact with the non-uniform contact layer, wherein the ultrasonic signals traverse the non-uniform contact layer. The sensor device includes a two-dimensional array of ultrasonic transducers, wherein the two-dimensional array of ultrasonic transducers is substantially flat, a non-uniform contact layer overlying the two-dimensional array of ultrasonic transducers, and a sensor processor. In one embodiment, the non-uniform contact layer includes regions of varying thickness. In one embodiment, the non-uniform contact layer includes a plurality of materials having different acoustic properties. In one embodiment, the sensor device is further configured to transmit the ultrasonic signals using the two-dimensional array of ultrasonic transducers based on a predefined non-uniformity template. At procedure 1220, reflected ultrasonic signals are received at the two-dimensional array of ultrasonic transducers.

At procedure 1230, non-uniformity data characterizing the non-uniform contact layer is obtained. In one embodiment, the sensor device further includes a memory device having the non-uniformity data stored thereon, wherein the sensor device is configured to obtain the non-uniformity data by reading the non-uniformity data from the memory device. In one embodiment, the non-uniformity data includes a time-of-flight register for ultrasonic transducers of the two-dimensional array of ultrasonic transducers. In one embodiment, the time-of-flight register is a time-of-flight map.

In one embodiment, in obtaining the non-uniformity data, procedure 1230 operates according to flow diagram 1300 of FIG. 13. With reference to FIG. 13, flow diagram 1300 of an example method for obtaining non-uniformity data characterizing the non-uniform contact layer is illustrated, according to an embodiment. It should be appreciated that flow diagram 1300 can be performed outside of the context of procedure 1230 of flow diagram 1300. For instance, flow diagram 1300 can be performed at a time of initialization or manufacturing of the sensor device, for generating non-uniformity data that can be stored in a memory of the sensor device for use during imaging. In other embodiments, flow diagram can be performed as a self-test, e.g., periodically or in response to an event.

At procedure 1310 of flow diagram 1300, ultrasonic signals are transmitted for a plurality of ultrasonic transducers of the two-dimensional array of ultrasonic transducers. At procedure 1320, the reflected ultrasonic signals for at least two different time-of-flights for the plurality of ultrasonic transducers are compared. At procedure 1330, a time-of-flight for each of the plurality of ultrasonic transducers is selected based on comparing the reflected ultrasonic signals for at least two different time-of-flights for the plurality of ultrasonic transducers. At procedure 1340, the non-uniformity data including a register of a selected time-of-flight for each of the plurality of ultrasonic transducers is generated.

In one embodiment, the sensor device is further configured to obtain the non-uniformity data at a plurality of times. In one embodiment, the sensor device is further configured to compare the non-uniformity data from the plurality of times and generate a change signal if the compare is outside a predefined range. In one embodiment, the change signal is indicative of a delamination in the sensor device. In another embodiment, the change signal is indicative of a surface defect.

With reference to FIG. 12, at procedure 1240, operating parameters of the sensor device are controlled based on the non-uniformity data. In one embodiment, the control of the operating parameters includes an adjustment for a difference in time-of-flight of the ultrasonic signals for at least one ultrasonic transducer of the two-dimensional array of ultrasonic transducers. In one embodiment, the adjustment for the difference in the time-of-flight of the ultrasonic signals includes an adjustment of timing parameters of a measurement window for the reflected ultrasonic signals. In one embodiment, the timing parameters of the measurement window are identical for all ultrasonic transducers, and the timing parameters of the measurements window are defined to cover differences in time-of-flight caused by the non-uniform contact layer. In another embodiment, the timing parameters of the measurement window are adapted for a plurality of ultrasonic transducers. In another embodiment, the control of the operating parameters includes an adjustment of timing of transmission of the ultrasonic signals for ultrasonic transducers of the two-dimensional array of ultrasonic transducers. In another embodiment, the control of the operating parameters includes an adjustment for a difference in reflection of the ultrasonic signals for at least one ultrasonic transducer of the two-dimensional array of ultrasonic transducers. In some embodiments, the control of the operating parameters may not be adjusted, for example, if the non-uniformity is too large to be corrected or is impossible for another reason.

At procedure 1250, an image of the object in contact with the non-uniform contact layer is generated based on the reflected ultrasonic signals, wherein the image is corrected for non-uniformity of the non-uniform contact layer. In some embodiments, correction of the image for the non-uniformity may not be performed or may not be possible.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:
1. A sensor device comprising:
 a two-dimensional array of ultrasonic transducers, wherein the two-dimensional array of ultrasonic transducers is substantially flat;
 a non-uniform contact layer overlying the two-dimensional array of ultrasonic transducers, wherein the non-uniform contact layer comprises a non-uniformity in a lateral direction of the contact layer such that different regions of the two-dimensional array of ultrasonic transducers correspond to regions of the contact layer having different transmission properties; and
 a sensor processor;
 wherein the sensor device is configured to:
  transmit ultrasonic signals using the two-dimensional array of ultrasonic transducers for reflection from an object in contact with the non-uniform contact layer, wherein the ultrasonic signals traverse the non-uniform contact layer;
  receive reflected ultrasonic signals at the two-dimensional array of ultrasonic transducers;
  obtain non-uniformity data characterizing the non-uniform contact layer;
  control operating parameters of the sensor device based on the non-uniformity data; and generate an image of the object in contact with the non-uniform contact layer based on the reflected ultrasonic signals, wherein the image is corrected for non-uniformity of the non-uniform contact layer.

2. The sensor device as recited in claim 1, wherein the control of the operating parameters comprises an adjustment for a difference in time-of-flight of the ultrasonic signals for at least one ultrasonic transducer of the two-dimensional array of ultrasonic transducers.

3. The sensor device as recited in claim 2, wherein the adjustment for the difference in the time-of-flight of the ultrasonic signals comprises an adjustment of timing parameters of a measurement window for the reflected ultrasonic signals.

4. The sensor device as recited in claim 3, wherein the timing parameters of the measurement window are identical for all ultrasonic transducers, and the timing parameters of the measurements window are defined to cover differences in time-of-flight caused by the non-uniform contact layer.

5. The sensor device as recited in claim 3, wherein the timing parameters of the measurement window are adapted for a plurality of ultrasonic transducers.

6. The sensor device as recited in claim 1, further comprising:
a memory device having stored thereon the non-uniformity data, wherein the sensor device is configured to obtain the non-uniformity data by reading the non-uniformity data from the memory device.

7. The sensor device as recited in claim 6, wherein the non-uniformity data comprises a time-of-flight register for ultrasonic transducers of the two-dimensional array of ultrasonic transducers.

8. The sensor device as recited in claim 7, wherein time-of-flight register is a time-of-flight map.

9. The sensor device as recited in claim 1, wherein the sensor device is further configured to:
transmit ultrasonic signals for a plurality of ultrasonic transducers of the two-dimensional array of ultrasonic transducers;
compare the reflected ultrasonic signals for at least two different time-of-flights for the plurality of ultrasonic transducers;
select a time-of-flight for each of the plurality of ultrasonic transducers based on comparing the reflected ultrasonic signals for at least two different time-of-flights for the plurality of ultrasonic transducers; and
generate the non-uniformity data comprising a register of the selected time-of-flight for each of the plurality of ultrasonic transducers.

10. The sensor device as recited in claim 1, wherein the sensor device is further configured to transmit the ultrasonic signals using the two-dimensional array of ultrasonic transducers based on a predefined non-uniformity template.

11. The sensor device as recited in claim 1, wherein the control of the operating parameters comprises an adjustment of timing of transmission of the ultrasonic signals for ultrasonic transducers of the two-dimensional array of ultrasonic transducers.

12. The sensor device as recited in claim 1, wherein the non-uniform contact layer comprises regions of varying thickness.

13. The sensor device as recited in claim 1, wherein the non-uniform contact layer comprises a plurality of materials having different acoustic properties.

14. The sensor device as recited in claim 1, wherein the control of the operating parameters comprises an adjustment for a difference in reflection of the ultrasonic signals for at least one ultrasonic transducer of the two-dimensional array of ultrasonic transducers.

15. The sensor device as recited in claim 1, wherein the sensor device is further configured to obtain the non-uniformity data at a plurality of times.

16. The sensor device as recited in claim 15, wherein the sensor device is further configured to compare the non-uniformity data from the plurality of times, and generate a change signal if the compare is outside a predefined range.

17. The sensor device as recited in claim 16, wherein the change signal is indicative of a delamination in the sensor device.

18. The sensor device as recited in claim 16, wherein the change signal is indicative of a surface defect.

19. A method for operating an ultrasonic fingerprint sensor with a non-uniform contact layer, the method comprising:
transmitting ultrasonic signals at the ultrasonic fingerprint comprising a two-dimensional array of ultrasonic transducers for reflection from an object in contact with the non-uniform contact layer, wherein the ultrasonic signals traverse the non-uniform contact layer, wherein the non-uniform contact layer comprises a non-uniformity in a lateral direction of the contact layer such that different regions of the two-dimensional array of ultrasonic transducers correspond to regions of the contact layer having different transmission properties;
receiving reflected ultrasonic signals at the two-dimensional array of ultrasonic transducers;
obtaining non-uniformity data characterizing the non-uniform contact layer;
controlling operating parameters of the ultrasonic fingerprint sensor based on the non-uniformity data; and
generating an image of the object in contact with the non-uniform contact layer based on the reflected ultrasonic signals, wherein the image is corrected for non-uniformity of the non-uniform contact layer.

20. The method as recited in claim 19, wherein the obtaining non-uniformity data characterizing the non-uniform contact layer comprises:
transmitting ultrasonic signals for a plurality of ultrasonic transducers of the two-dimensional array of ultrasonic transducers;
comparing the reflected ultrasonic signals for at least two different time-of-flights for the plurality of ultrasonic transducers;
selecting a time-of-flight for each of the plurality of ultrasonic transducers based on comparing the reflected ultrasonic signals for at least two different time-of-flights for the plurality of ultrasonic transducers; and
generating the non-uniformity data comprising a register of a selected time-of-flight for each of the plurality of ultrasonic transducers.

21. A non-transitory computer readable storage medium having computer readable program code stored thereon for causing a computer system to perform a method for operating an ultrasonic fingerprint sensor with a non-uniform contact layer, the method comprising:
transmitting ultrasonic signals at the ultrasonic fingerprint comprising a two-dimensional array of ultrasonic transducers for reflection from an object in contact with the non-uniform contact layer, wherein the ultrasonic signals traverse the non-uniform contact layer, wherein the ultrasonic signals are transmitted based on a predefined non-uniformity template, and wherein the non-uniform contact layer comprises a non-uniformity in a lateral direction of the contact layer such that different regions of the two-dimensional array of ultrasonic transducers correspond to regions of the contact layer having different transmission properties;

receiving reflected ultrasonic signals at the two-dimensional array of ultrasonic transducers;

obtaining non-uniformity data characterizing the non-uniform contact layer;

controlling operating parameters of the ultrasonic fingerprint sensor based on the non-uniformity data, wherein the controlling the operating parameters comprises adjusting for a difference in reflection of the ultrasonic signals for at least one ultrasonic transducer of the two-dimensional array of ultrasonic transducers; and generating an image of the object in contact with the non-uniform contact layer based on the reflected ultrasonic signals, wherein the image is corrected for non-uniformity of the non-uniform contact layer.

* * * * *